United States Patent [19]
Livingston et al.

[11] Patent Number: 5,584,813
[45] Date of Patent: Dec. 17, 1996

[54] SUBCUTANEOUS INJECTION SET

[75] Inventors: John H. Livingston, Marina Del Rey; April A. Konopka, San Dimas, both of Calif.

[73] Assignee: MiniMed Inc., Sylmar, Calif.

[21] Appl. No.: 477,810

[22] Filed: Jun. 7, 1995

[51] Int. Cl.⁶ ............................................. A61M 5/32
[52] U.S. Cl. ..................... 604/177; 604/280; 604/164; 604/167
[58] Field of Search ............................ 604/164–167, 604/174–178, 180, 264–280

[56] References Cited

U.S. PATENT DOCUMENTS

| | | |
|---|---|---|
| 4,562,751 | 1/1986 | Nason et al. . |
| 4,678,408 | 7/1987 | Nason et al. . |
| 4,685,903 | 8/1987 | Cable et al. . |
| 4,710,176 | 12/1987 | Quick ........................ 604/177 |
| 4,755,173 | 7/1988 | Konopka et al. . |
| 5,176,662 | 1/1993 | Batholomew et al. . |
| 5,254,106 | 10/1993 | Feaster ........................ 604/272 |
| 5,257,980 | 11/1993 | Van Antwerp et al. . |
| 5,360,416 | 11/1994 | Ausherman et al. ........................ 604/272 |
| 5,390,671 | 2/1995 | Lord et al. . |
| 5,391,250 | 2/1995 | Cheney, II et al. . |
| 5,425,717 | 6/1995 | Mohiuddin ........................ 604/177 X |

*Primary Examiner*—Sam Rimell
*Assistant Examiner*—Robert V. Racunas
*Attorney, Agent, or Firm*—Kelly Bauersfeld & Lowry

[57] ABSTRACT

A subcutaneous injection set is disclosed of the type having an insertion needle for quick and easy subcutaneous placement of a soft cannula through which medication can be delivered to a patient. In one preferred form, the subcutaneous injection set comprises a base adapted for press-on attachment to the skin of a patient at a selected infusion site. The base includes a connector sleeve for connecting a length of infusion tubing to the soft cannula. The soft cannula is threaded through an eye formed near the distal end of the insertion needle which is mounted on a collapsible injector that is detachably mounted to the base. The base is positioned on the patient's skin, the injector is collapsed by pressing toward the patient's skin whereby the insertion needle pierces the skin for transcutaneous cannula placement. The press stroke of the insertion needle is sufficient to unthread the cannula therefrom, whereupon the injector can be retracted to withdraw the insertion needle from the patient. The needle carrier can then be detached from the base and discarded.

28 Claims, 2 Drawing Sheets

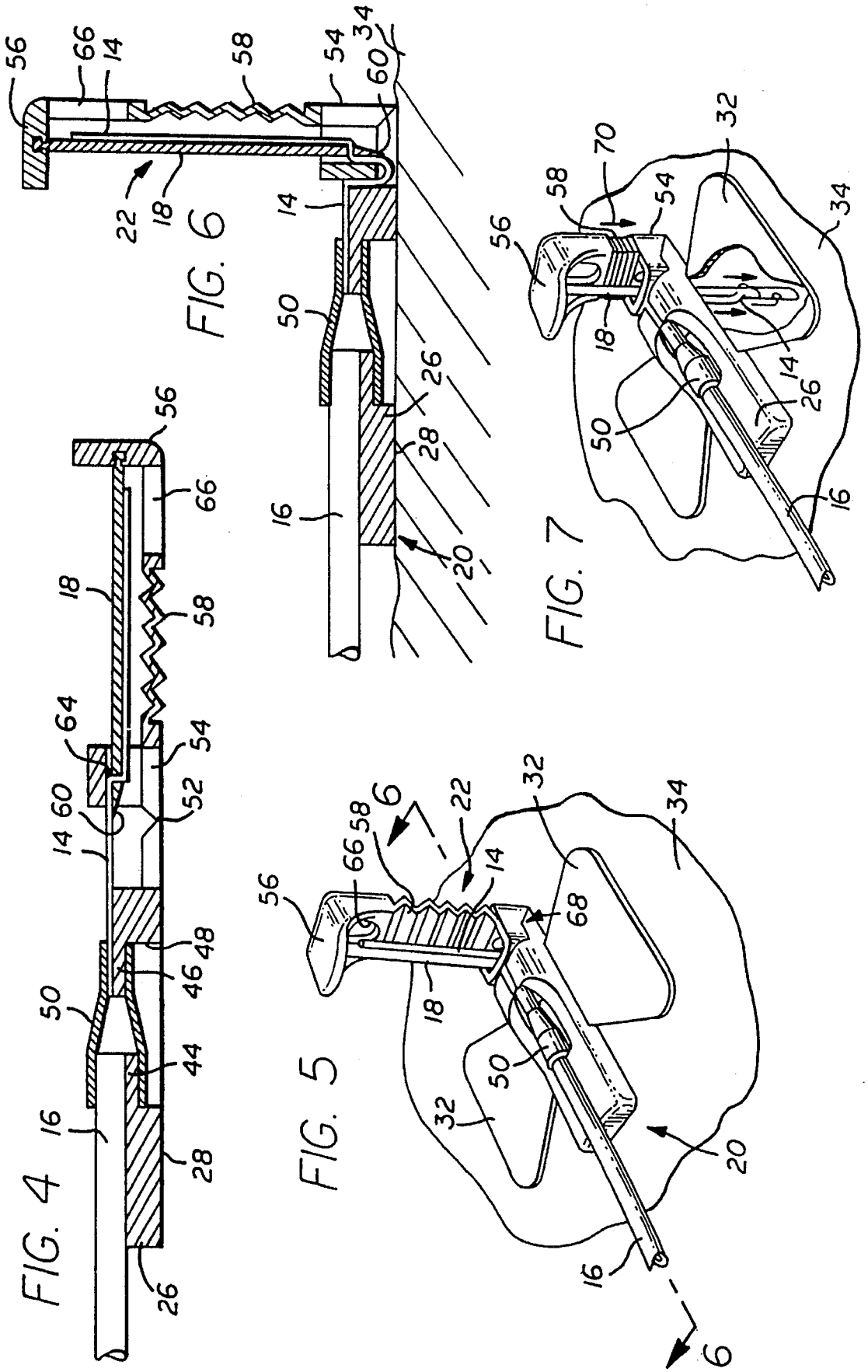

SUBCUTANEOUS INJECTION SET

BACKGROUND OF THE INVENTION

This invention relates generally to injection devices for use with an external infusion system for subcutaneous delivery of a selected medication or other therapeutic fluid to a patient. More particularly, this invention relates to an improved subcutaneous injection set for quick and easy transcutaneous placement of a soft cannula through the skin of a patient at a selected medication infusion site.

Subcutaneous injection sets are generally known in the medical arts for use in the administration of a selected medication or other therapeutic fluid to a desired subcutaneous infusion site located beneath the skin of a patient. Such injection set commonly includes a tubular cannula or catheter which is supported by and protrudes from a compact housing adapted to receive the infusion fluid via delivery or infusion tubing which is suitably connected to other components of the fluid infusion system.

The subcutaneous injection set normally includes an insertion needle which is assembled with the soft cannula and is adapted to pierce the patient's skin for transcutaneous cannula placement. The insertion needle is thereafter withdrawn to leave the cannula in place for subcutaneous fluid infusion. Exemplary subcutaneous injection sets of this general type are described and claimed in U.S. Pat. Nos. 4,755,173; 5,176,662; and 5,257,980, which are incorporated by reference herein. Such subcutaneous injection sets are commonly used with compact medication infusion pumps for programmable administration of medication such as insulin, wherein exemplary infusion pumps of this general type are described in U.S. Pat. Nos. 4,562,751; 4,678,408; and 4,685,903, which are incorporated by reference herein.

In the past, subcutaneous injection sets have typically been constructed from multiple assembled components for receiving and supporting the infusion tubing in flow communication with the soft cannula, in combination with the insertion needle for subcutaneous cannula placement. Accordingly, while these prior injection sets have functioned in a satisfactory manner, production thereof has been relatively costly and tedious.

The present invention provides a significantly improved subcutaneous injection set which can be manufactured quickly and easily from a comparatively minimum number of parts which when assembled provide for quick and easy subcutaneous cannula placement.

SUMMARY OF THE INVENTION

In accordance with the invention, an improved subcutaneous injection set is provided for quick and easy subcutaneous placement of a soft cannula at a selected medication infusion site on the body of a patient. The injection set comprises a soft cannula mounted in flow communication with a length of infusion tubing, in combination with a collapsible and disposable injector having an insertion needle for transcutaneous cannula placement. The cannula is adapted for threading through an eye formed in the needle, whereupon the injector can be placed against the patient's skin and collapsed so that the needle carries the cannula to the desired transcutaneous site. The cannula unthreads from the needle during insertion, so that the needle can be retracted from the patient to leave the cannula in place. The injector, including the insertion needle, can then be discarded.

In one preferred form, the injection set includes a base having a main body adapted for nested or seated support of one end of a length of infusion tubing. A connector sleeve formed preferably as a shrink-fit structure is provided for securing the infusion tubing to the main body, in flow communication with a soft cannula. In addition, the base includes a pair of outwardly protruding attachment wings adapted for press-on attachment to the patient's skin at a selected medication infusion site.

The main body of the injection set base is connected to the injector having the insertion needle mounted thereon, as by insert molding or the like. The injector is hingedly or pivotally connected to the base, so that the insertion needle can be oriented with a distal end defining a sharp tip pointed toward and in close proximity to the selected infusion site. A distal or free end of the cannula is threaded through the eye formed in said needle near the distal end thereof. The injector is oriented with the insertion needle pointing generally toward the patient's skin, whereupon the needle carrier is longitudinally collapsed to cause the needle to pierce the patient's skin and thereby carry the soft cannula to the desired subcutaneous position. The length of the injector insertion stroke is sufficient to unthread the cannula from the insertion needle. Engageable stop surfaces are desirably provided on the base and the injector to facilitate retention of the needle in a desired orientation during this insertion step. Thereafter, the injector can be manually withdrawn to retract the insertion needle from the patient at which time the injector is detachably removed from the base and discarded.

Other features and advantages of the present invention will become more apparent from the following detailed description, taken in conjunction with the accompanying drawings which illustrate, by way of example, the principles of the invention.

DESCRIPTION OF THE DRAWINGS

The accompanying drawings illustrate the invention. In such drawings:

FIG. 4 is a longitudinal sectional view taken generally on the line 4—4 of FIG. 3;

FIG. 5 is a perspective view depicting the injection set mounted onto the skin of a patient, and with an injector oriented for transcutaneous cannula placement;

FIG. 6 is a sectional view taken generally on the line 6—6 of FIG. 5; and

FIG. 7 is a perspective view similar to FIG. 5, and depicting collapse of the injector for transcutaneous cannula placement.

DETAILED DESCRIPTION OF THE PREFERRED EMBODIMENT

Figure 1:
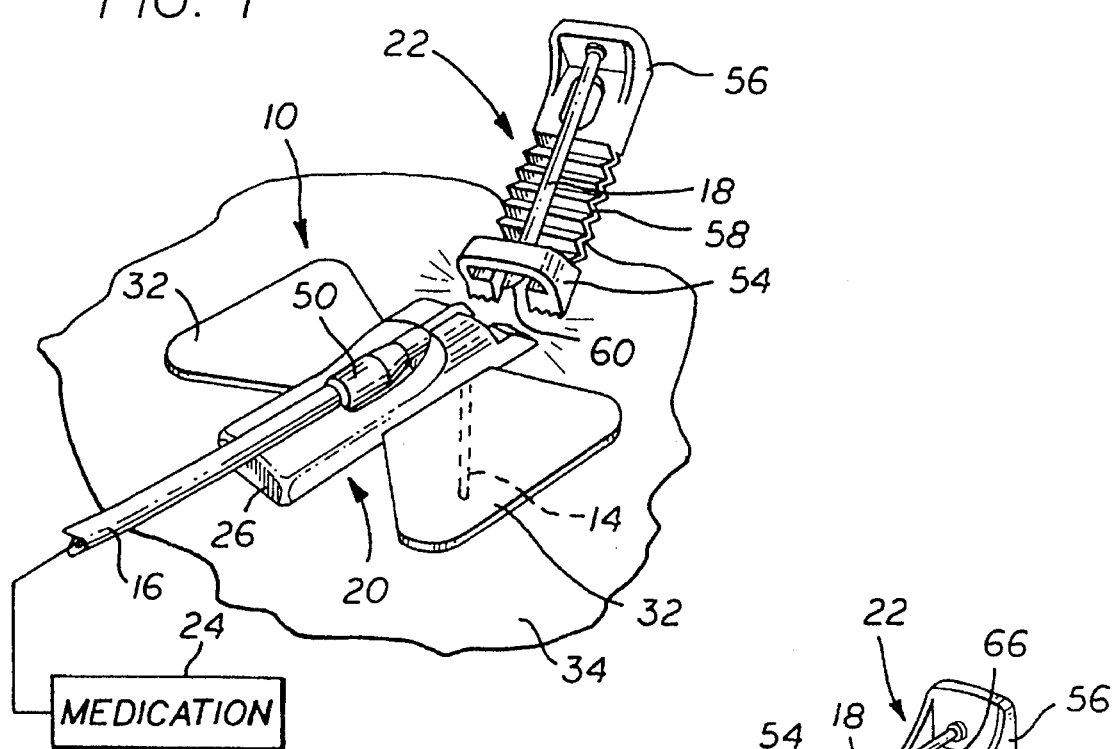
FIG. 1 is an exploded perspective view illustrating use of the subcutaneous injection set of the present invention for transcutaneous placement of a medication infusion cannula.

As shown in the exemplary drawings, an improved subcutaneous injection set referred to generally by the reference numeral 10 is provided for subcutaneous delivery of a selected medication or other therapeutic infusion fluid to a patient. The improved injection set 10 comprises a simplified housing structure for supporting a soft cannula 14 and a length of infusion tubing 16 in flow communication with each other, in combination with an insertion needle 18 for placing the cannula 14 transcutaneously at a selected medication infusion site. In accordance with one aspect of the invention and as shown in the illustrative drawings, the simplified housing structure of the injection set 10 generally comprises a base 20 and a related injector 22 which can be manufactured as a convenient unitary plastic molding.

The subcutaneous injection set 10 of the present invention is particularly designed for use in the subcutaneous delivery of a selected medication such as insulin to a patient, wherein the infusion tubing 16 is connected to an appropriate supply or source 24 of the selected medication, such as an external programmable medication infusion pump of the type described in U.S. Pat. Nos. 4,562,751; 4,678,408; and 4,685,903, which are incorporated by reference herein. The injection set 10 comprises a relatively inexpensive and lightweight device that can be mounted onto the skin of a patient in a selected and convenient inconspicuous location, with the soft cannula 14 being transcutaneously placed quickly and easily, and providing a relatively comfortable and substantially painless transcutaneous medication infusion pathway.

As shown in FIGS. 1–4, the base 20 of the injection set 10 comprises a central or main body 26 formed in a generally rectangular configuration with a substantially flat or planar bottom surface 28 (FIG. 4) and a sufficient thickness to provide a relatively stiff or rigid structure. The opposite side edges of the main body 26 are joined along hinge lines 30 to a pair of outwardly protruding and comparatively thinner attachment wings 32. The attachment wings 32 have an underside surface adapted for carrying an adhesive film (not shown) or the like so that the attachment wing s 32 can be adhesively affixed or attached to the patient's skin 34 (FIG. 1) when the base 20 is pressed-mounted onto the patient's skin. As is known in the art, the adhesive film on the underside surfaces of the attachment wings 32 typically comprises a pressure sensitive film, and is normally covered by peel-off paper strips (not shown) prior to use.

Figure 2:
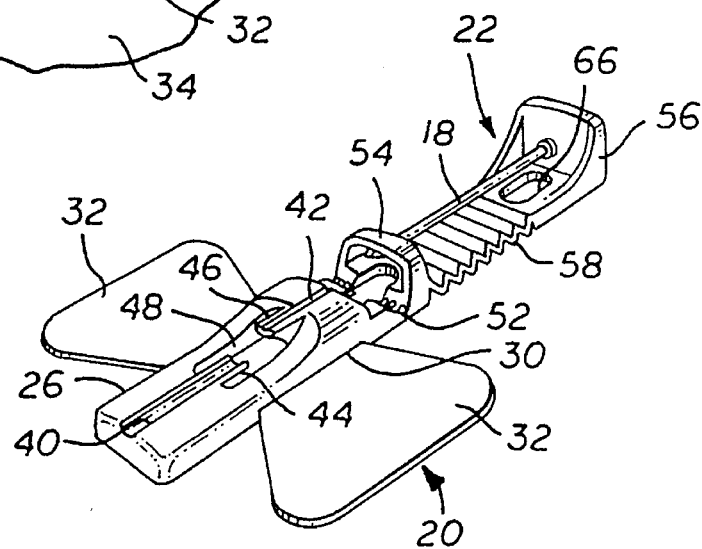
FIG. 2 is a perspective view illustrating portions of the subcutaneous injection set, prior to assembly with a soft cannula and related infusion tubing.
Figure 3:
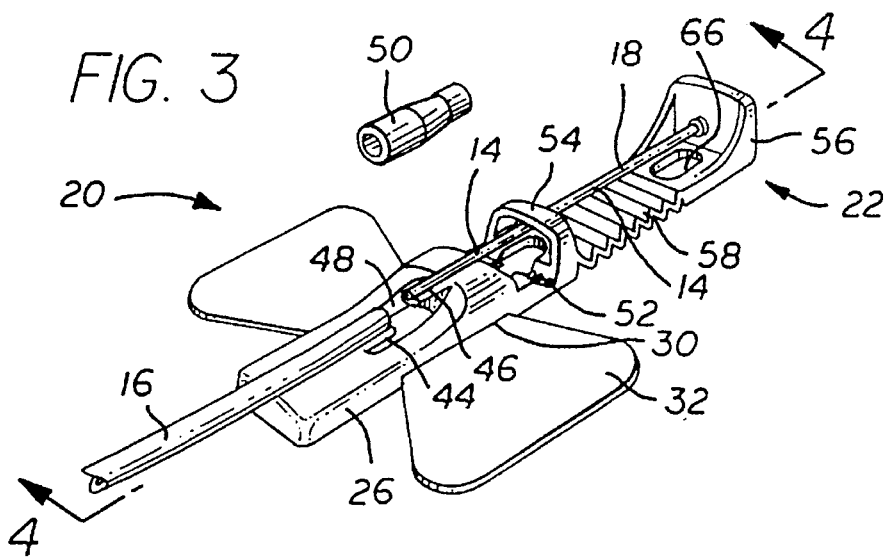
FIG. 3 is an exploded perspective view similar to FIG. 2, and depicting a connector sleeve for use in assembly of the soft cannula and related infusion tubing.

The upper or top surface of the main body 26 includes a pair of elongated part-cylindrical recesses 40 and 42 (FIG. 2) for respective nested reception of the ends of the infusion tubing 16 and the soft cannula 14 (FIG. 3). As shown best in FIGS. 2 and 3, these recesses 40 and 42 are disposed approximately in-line with each other to support a downstream or distal end of the infusion tubing 16 in relatively closely spaced relation with the upstream or proximal end of the soft cannula 14. The adjacent ends of the recesses 40, 42 are defined by relatively short protrusions 44 and 46, respectively, which extend part-way into a central opening 48 formed in the main body 26. These protrusions 44, 46 provide convenient structures in approximate alignment with each other, and in closely spaced relation, so that the adjacent ends of the infusion tubing 16 and soft cannula 14 can be interconnected in flow communication with each other by a short cylindrical connector sleeve 50 (FIG. 3). This connector sleeve 50 is conveniently constructed from a shrink-to-fit material mounted about the protrusions 44, 46 (FIGS. 2–4) to provide a mechanical structure which secures the infusion tubing 16 and the soft cannula 14 to the main body 26 of the injection set base 20. This shrink-fit sleeve may be provided in various forms, such as a heat shrinkable medical grade tubing of the type marketed by Raychem Corporation of Menlo Park, Calif. under the product designation MT-100 (polyvinylidene fluoride tubing).

A forward or nose end of the main body 26 of the base 20 is joined to the injector 22 at a hinge line 52. This hinge line 52 is conveniently perforated to permit detachment of the injector 22 from the base 20, as will be described in more detail. As shown, the injector 22 comprises a relatively rigid stop member 54 adjacent to the base 20, and a relatively rigid press plate 56, with a longitudinally collapsible segment 58 extending therebetween and shown in the illustrative drawings in the form of a longitudinally extending series of corrugations or folds.

The press plate 56 of the injector 22 supports the insertion needle 18, which may be conveniently attached thereto as by insert molding or the like. From the press plate 56, the insertion needle 18 projects toward the base 20, terminating in a distal end defined by a sharpened tip 60 exposed protectively within an open loop defined by the stop member 54. An eye 64 (FIG. 4) is formed in the insertion needle 18 near the sharpened tip 60 for thread-through passage of the soft cannula 14. From the eye 64, the cannula 14 extends generally alongside the insertion needle 18, between the needle and the underlying collapsible segment 58, terminating in a distal or free end disposed near the press plate 56 and visible through a priming port 66.

In use, as viewed in FIG. 5, the base 20 of the subcutaneous injection set 10 is mounted onto the patient's skin 34 by press-on attachment of the wings 32. The injector 22 is then manually pivoted to a selected angular orientation, typically oriented generally perpendicular, relative to the patient's skin and the related base 20. Interengaging surfaces of the stop member 54 and the base 20 (referenced in FIG. 5 by arrow 68) permit stable positioning and retention of the injector 22 at the desired orientation. In this orientation, the infusion tubing 16 and related soft cannula 14 can be primed with medication, until medication droplets are observed exiting the soft cannula 14, as visually observed through the priming port 66.

With the injection set fully primed, the cannula 14 is quickly and easily placed subcutaneously by press-collapsing the injector 22 so that the needle 18 carries the cannula 14 to the desired subcutaneous position. That is, as viewed in FIGS. 5–7, the press-plate 56 is manually collapsed by a pressing motion toward the patient's skin, as referenced by arrow 70 in FIG. 7, to cause the collapsible segment 58 to compress upon itself and allow the insertion needle 18 to pierce the patient's skin. During this piercing stroke motion, the needle 18 carries the cannula 14 to the subcutaneous injection site. The length of the needle downward press stroke, in comparison with the length of the cannula 14 which projects beyond the needle eye 64, is chosen so that the cannula 14 will unthread from the needle upon full downward stroke motion of said needle.

The insertion needle 18 can then be manually withdrawn from the patient's skin by pulling upwardly on the injector 22 to re-extend the collapsible segment 58, thereby leaving the cannula 14 at the desired subcutaneous injection site. The injector 22, with the insertion needle 18 thereon, can then be detachably removed or separated from the base 20, as viewed in FIG. 1, by tearing injector 22 from the base 20 at the perforated hinge line 52. In this regard, the geometry of the components in the vicinity of the hinge line 52 may be suitably contoured to avoid sharp edges in contact with patient skin. The injector 22 and related insertion needle 18 can then be properly discarded, leaving the base 20 in place for long term transcutaneous medication infusion via the soft cannula 14.

In accordance with one aspect of the invention, the base 20 and injector 22 may be conveniently formed from a single unitary injection molded component. The unitary component, as viewed in FIG. 2, is quickly and easily assembled with other requisite components of the injection set, as viewed in FIG. 3, resulting in an economical and easy-to-use injection set device. Alternately, the base 20 can be omitted, in which case a distal end of the infusion tubing 16 would be appropriately connected in-line with the flexible cannula 14, and a separate injector with insertion needle thereon used to transcutaneously place the cannula. Such separate injector would include a modified stop member 54 shaped for stable seating against the patient's skin during cannula placement, after with the infusion tubing 16 and cannula 14 can be secured to the patient's skin by a strip of adhesive tape or the like.

A variety of modifications and improvements to the improved subcutaneous injection set of the present invention will be apparent to those skilled in the art. For example, it will be understood that the injection set can be used for subcutaneous placement of medical devices other than or in addition to a soft cannula. Such alternative devices would include subcutaneous sensors of the type described in U.S. Pat. Nos. 5,390,671 and 5,391,250, which are incorporated by reference herein. Other subcutaneous devices could include, for example, an optical fiber or the like. Accordingly, no limitation on the invention is intended by way of the foregoing description and accompanying drawings, except as set forth in the appended claims.

What is claimed is:

1. A subcutaneous injection set for subcutaneous placement of a distal end of a soft flexible cannula at a selected injection site, said injection set comprising:

a longitudinally collapsible injector; and an insertion needle carried by said injector and having an eye formed therein for threaded reception of said distal end of said cannula;

said injector being longitudinally collapsible with one end thereof placed against the skin of a patient at a selected injection site for movement of said insertion needle through an insertion stroke to cause said needle to pierce the patient's skin and subcutaneously place said distal end of said cannula, said insertion stroke being of sufficient length to cause said cannula to unthread from said needle, said longitudinally extensible injector being movable through a return stroke to withdraw said insertion needle from the patient's skin.

2. The subcutaneous injection set of claim 1 wherein said insertion needle is connected to said injector by insert molding.

3. The subcutaneous injection set of claim 1 wherein said injector has a priming port formed therein to permit observation of the cannula distal end.

4. The subcutaneous injection set of claim 1 further including means for connecting a proximal end of said cannula to a length of infusion tubing.

5. The subcutaneous injection set of claim 4 wherein said connecting means comprises a shrink-fit sleeve.

6. The subcutaneous injection set of claim 1 further including a base adapted for placement onto a patient's skin at a selected injection site, said injector being removably carried by said base, said injector with said insertion needle thereon being separable from said base to leave said base on the patient's skin with the distal end of the cannula placed subcutaneously at the selected injection site.

7. The subcutaneous injection set of claim 1 wherein said base and said injector are formed as a unitary plastic molding.

8. The subcutaneous injection set of claim 6 wherein said injector is hingedly connected to said base.

9. The subcutaneous injection set of claim 6 wherein said injector is connected to said base by a perforated tear-away hinge.

10. The subcutaneous injection set of claim 6 wherein said injector includes a first segment removably connected to said base, a second segment having said insertion needle mounted thereon to extend therefrom in a direction generally toward said first segment, and a longitudinally collapsible third segment connected between said first and second segments.

11. The subcutaneous injection set of claim 10 wherein said first segment is hingedly connected to said base and cooperates therewith to define stop surfaces to permit retention of said insertion needle at a selected orientation relative to the patient's skin when said base is mounted on the patient's skin.

12. The subcutaneous injection set of claim 6 further including means for connecting a proximal end of said cannula to a length of infusion tubing.

13. The subcutaneous injection set of claim 12 wherein said base has an opening formed therein and defines generally aligned protrusions projecting into said opening in spaced relation to each other, one end of said infusion tubing and said cannula proximal end being supported respectively on said protrusions, and wherein said connecting means comprises a sleeve interconnecting said one end of said infusion tubing with said cannula proximal end, said sleeve being wrapped about said protrusions to secure said infusion tubing and said cannula to said base.

14. The subcutaneous injection set of claim 13 wherein said sleeve is a shrink-fit sleeve.

15. The subcutaneous injection set of claim 6 wherein said base includes at least one outwardly projecting wing for adhesive attachment to the patient's skin.

16. The subcutaneous injection set of claim 1 wherein said injector includes a first portion adapted for placement against the patient's skin at the selected injection site, a second segment having said insertion needle mounted thereon to extend therefrom in a direction generally toward said first segment, and a longitudinally collapsible third segment connected between said first and second segments.

17. A subcutaneous injection set, comprising:

a soft cannula having a proximal end and a distal end;

a length of infusion tubing;

means for connecting one end of the infusion tubing to said cannula proximal end;

an injector having a first segment adapted for placement against a patient's skin at a selected injection site, a second segment having an insertion needle mounted thereon and extending therefrom in a direction generally toward said first segment, and a longitudinally collapsible third segment connected between said first and second segments;

said insertion needle having an eye formed therein with said distal end of said cannula threaded therethrough;

said injector being collapsible for movement through an insertion stroke to cause said needle to pierce the patient's skin and subcutaneously place said distal end of said cannula, said insertion stroke being of sufficient length to cause said cannula to unthread from said needle, said injector being movable through a return stroke to withdraw said insertion needle from the patient's skin.

18. The subcutaneous injector set of claim 17 further including a base adapted for attachment to the patient's skin, said injector being hingedly and removably connected to said base, said injector with said insertion needle thereon being separable from said base to leave said base on the patient's skin with the distal end of the cannula placed subcutaneously at the selected injection site.

19. The subcutaneous injection set of claim 18 wherein said injector is connected to said base by a perforated tear-away hinge.

20. The subcutaneous injection set of claim 18 wherein said first segment is hingedly connected to said base and cooperates therewith to define stop surfaces to permit retention of said insertion needle at a selected orientation relative to the patient's skin when said base is mounted on the patient's skin.

21. The subcutaneous injection set of claim 17 wherein said injector has a priming port formed therein to permit observation of the cannula distal end.

22. The subcutaneous injection set of claim 17 wherein said connecting means comprises a shrink-fit sleeve.

23. A subcutaneous injection set, comprising:

a base adapted for placement onto a patient's skin at a selected injection site;

a soft cannula defining a distal end for subcutaneous placement at the injection site;

an injector; and an insertion needle carried by said injector and having an eye formed therein with said cannula distal end threaded therethrough;

said injector supporting said insertion needle for movement through an insertion stroke relative to said base to cause said needle to pierce the patient's skin and subcutaneously place said distal end of said cannula, said insertion stroke being of sufficient length to cause said cannula to unthread from said needle, said injector being movable through a return stroke relative to said base to withdraw said insertion needle from the patient's skin to leave said cannula distal end placed subcutaneously at the selected injection site.

24. A subcutaneous injection set for subcutaneous placement of a distal end of a medical device at a selected injection site, said injection set comprising:

a longitudinally deformable injector; and an insertion needle carried by said injector and having an eye formed therein for threaded reception of said distal end of said medical device;

said injector being longitudinally movable with one end thereof placed against the skin of a patient at a selected injection site for movement of said insertion needle through an insertion stroke to cause said needle to pierce the patient's skin and subcutaneously place said distal end of said medical device, said insertion stroke being of sufficient length to cause said medical device to unthread from said needle, said injector being longitudinally movable through a return stroke to withdraw said insertion needle from the patient's skin.

25. The subcutaneous injection set of claim 23 further including a base adapted for placement onto a patient's skin at a selected injection site, said injector being removably carried by said base, said injector with said insertion needle thereon being separable from said base to leave said base on the patient's skin with the distal end of said medical device subcutaneously placed at the injection site.

26. The subcutaneous injection set of claim 24 wherein said injector is connected to said base by a perforated tear-away hinge.

27. The subcutaneous injection set of claim 24 wherein said injector includes a first segment removably connected to said base, a second segment having said insertion needle mounted thereon to extend therefrom in a direction generally toward said first segment, and a longitudinally collapsible third segment connected between said first and second segments.

28. A method of subcutaneously placing a distal end of a medical device at a selected injection site, said method comprising the steps of:

providing a longitudinally deformable injector having an insertion needle carried thereon, said needle having an eye therein;

threading the distal end of the medical device through the eye of the insertion needle;

placing the injector against the skin of a patient at a selected injection site;

longitudinally moving the injector against the patient's skin through an insertion stroke to cause the needle to pierce the skin and subcutaneously place the distal end of the medical device, wherein the insertion stroke is of sufficient length to cause the medical device to unthread from the needle; and withdrawing the injector to remove the insertion needle from the patient to leave the distal end of the medical device subcutaneously at the selected injection site.

* * * * *